United States Patent [19]

Smith et al.

[11] 4,229,169
[45] Oct. 21, 1980

[54] DENTAL PROSTHESES FITTING

[76] Inventors: Peter J. Smith, 6 Kegworth St.; Kishor Bava, 246 High St., both of Eltham, New Zealand

[21] Appl. No.: 959,149

[22] Filed: Nov. 9, 1978

[30] Foreign Application Priority Data

Nov. 17, 1977 [NZ] New Zealand ................. 185708

[51] Int. Cl.³ ........................................... A61C 8/00
[52] U.S. Cl. ................................................ 433/174
[58] Field of Search ........................ 32/10 A; 433/174

[56] References Cited

U.S. PATENT DOCUMENTS

| | | | |
|---|---|---|---|
| 3,672,058 | 6/1972 | Nikoghossian | 32/10 A |
| 3,717,932 | 2/1973 | Brainin | 32/10 A |

Primary Examiner—Robert Peshock
Attorney, Agent, or Firm—Holman & Stern

[57] ABSTRACT

A technique of fitting prosthetic teeth whereby a hole is drilled and a screw compatible with the bone of the jaw bone is located within the hole. The screw is characterized by having from the head end thereof a hole into which the post which is to fit the prosthetic tooth thereto is receivable. The method then allows the post to be located for the taking of impressions and for the subsequent removal of the post for refitting after the prosthetic tooth has been prepared and has been associated with portions of said post. Ideally the post and the tooth are only fitted after a suitable healing period following the screwing of the screw. The invention also consists in apparatus and tools related to such a method.

10 Claims, 6 Drawing Figures

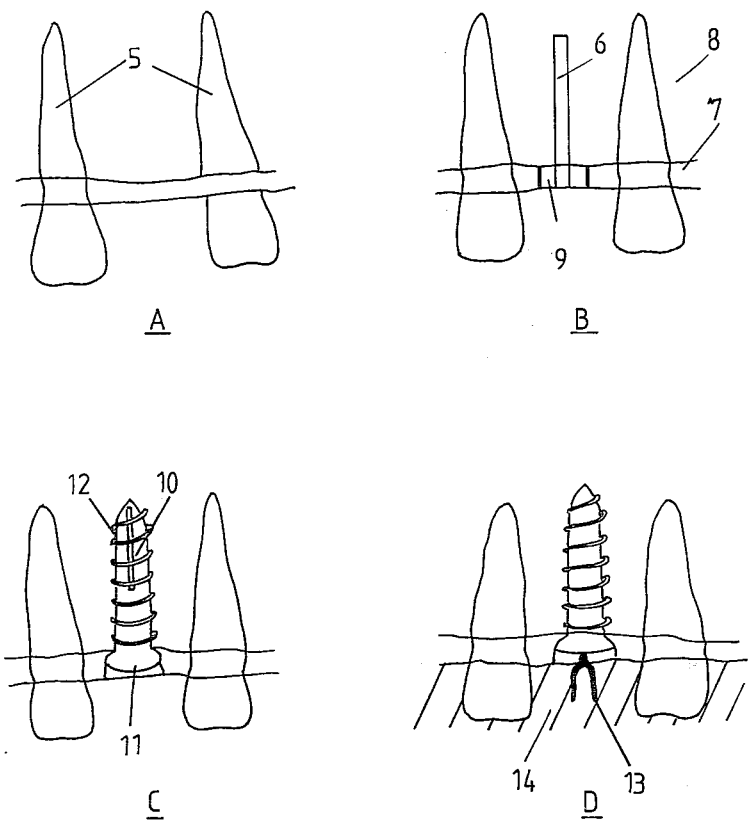
FIG.6.
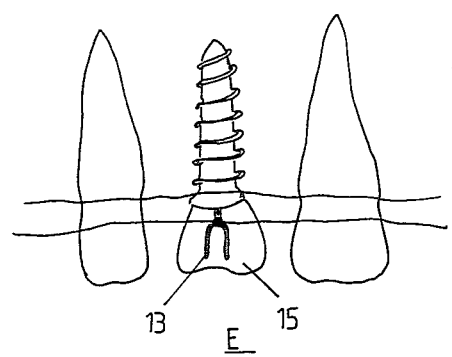

DENTAL PROSTHESES FITTING

BACKGROUND OF THE INVENTION

1. Field of the Invention

The present invention relates to apparatus, means and methods applicable to the fitting of prosthetic teeth, whereby the main bone anchoring device is a bone compatible screw which has a hole extending from the head end thereof into which the connecting post to which the prosthetic tooth is attached or is to be attached can be adhesively received.

2. Description of the Prior Art

Often in dentistry, when a tooth has to be removed, there is a functional, dictional and an aesthetic desirability that a "tooth" be substituted in place of the tooth for which even the roots may have been removed. In this regard, various anchoring techniques have been devised and some of the most sophisticated techniques are those disclosed in New Zealand Pat. Nos. 158,376 and 163,118 to AGA AB. These techniques however, are complicated and would be unlikely to find widespread acceptance owing to the fact that treatment must take place over a prolonged period. There is, therefore, some need to provide a method, means and apparatus therefor which will enable the fitting of an artificial tooth within a short period.

It is, therefore, an object of the present invention to provide apparatus, means and methods which will go at least some way to meet the abovementioned desiderata, or which will at least provide the public with a useful choice.

BRIEF SUMMARY OF THE INVENTION

Accordingly, in one aspect the present invention consists in a screw for location in a jaw bone, said screw being formed from a material compatible with the bone of the jaw bone and including axially extending from the head end of said screw a hole.

Preferably said screw is self-tapping. Preferably said screw includes an axial groove or some equivalent "anti-rotation" means. Preferably said screw is formed from vitallium. Preferably said hole does not extend for the full length of the screw. Preferably said hole is not threaded. Preferably said hole includes a knurl like surface.

In a further aspect, the present invention consists in combination a screw in accordance with the present invention and a post member having a portion capable of being anchored by adhesion within said hole. Preferably said post is formed from a metal and preferably the end of said post which is to be located inside the artificial tooth formed from any appropriate material, for example, a plastic, is bifurcated.

Preferably said screw and/or said post are substantially as hereinafter described.

In a further aspect, the invention consists in a tissue cutting apparatus comprising means to locate the apparatus with respect to a hole in a jaw bone for said screw in accordance with the present invention and means capable when said apparatus is revolved about an axis coincident with the axis of said hole of cutting tissue concentrically about said hole and upon axial movement towards said jaw bone to said jaw bone.

Preferably said apparatus is substantially as hereinafter described.

Preferably said apparatus is in combination or adapted to be used in combination with a screw in accordance with the present invention and for this reason preferably said collar cutting edges are adapted to cut a core substantially identical in diameter to the head of said screw.

In a further aspect the present invention consists in a method of fitting an artificial prosthetic tooth comprising the steps of:

1. drilling a hole in the jaw bone at or adjacent the position that the tooth to be replaced had its roots,
2. locating by screwing into said hole a screw formed from a material compatible with the bone of the jaw bone into said jaw bone, said screw including axially from the head end thereof a hole,
3. inserting a post at least partly into said hole of said screw, and post being of a kind that when partly received within the hole of said screw is capable of having the protruding portion thereof wholly received within the prosthetic tooth,
4. taking an impression from said post when located within said hole of the screw
5. preparing the artificial tooth and fitting the same to said post when said post is not received within said screw, the fitting being to the normally protruding region thereof when said post is received within said screw hole, and
6. subsequently adhering the portion of said post not received within the artificial tooth into the hole of said screw to thus locate the artificial tooth affixed thereto.

Preferably said screw is screwed into a non-threaded drilled hole. Preferably the post is removed with the impression. Preferably the adhesion is effected using normal dental adhesives.

Preferably the drilling is effected using apparatus or a drill in accordance with the present invention which removes a core of soft tissue to allow access for the screw head to and/or into said jaw bone.

Preferably said method is substantially as hereinafter described in detail.

In still a further aspect, the invention consists in an assembly of a screw locatable in a jaw bone, said screw being formed from a material compatible with the bone of the jaw bone and including axially from the head end of said screw a blind hole and a post member having a portion thereof anchored by adhesion within said hole, said post members being of dimensions for having the portions, thereof not received within said hole of the screw of being received within a prosthetic tooth.

Preferably said screw and/or post as substantially as hereinbefore defined.

BRIEF DESCRIPTION OF THE DRAWINGS

The invention consists in the foregoing and also envisages constructions of which the following gives examples.

One preferred form of the present invention will now be described with reference to the accompanying drawings in which FIG. 6 is a diagrammatic view showing the stages of the fitting of an artificial tooth to a patient's mouth, the drawings of FIG. 6 being identified by letters A to E.

DETAILED DESCRIPTION OF THE PREFERRED FORMS OF THE INVENTION

Figure 1:
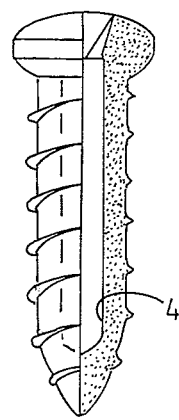
FIG. 1 is a side elevation of a screw in accordance with the present invention showing part thereof in section.
Figure 2:
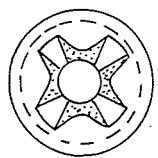
FIG. 2 is an end view of the screw of FIG. 1 looking down at the head thereof.
Figure 4:
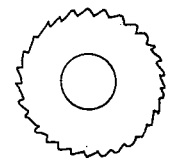
FIG. 4 is a view AA of said apparatus of FIG. 3.
Figure 5:
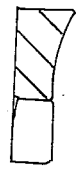
FIG. 5 is a section of part of the tissue cutting means of the apparatus of FIGS. 3 and 4.

The screw in accordance with the present invention has preferably been formed from the metal vitallium which is known to be both tissue and bone compatible. The actual screw is preferably a self tapping screw of the kind shown in FIGS. 1 and 2. Ideally the screw is one having a Phillips head and an axially extending bore leading therefrom for approximately two-thirds of the length of the screw. Ideally the screw length will be such as to be suitable for a particular jaw bone and for this reason, therefore, a variety of different sizes should be provided; for the present purposes, in order to understand the present invention, no sizes in particular need be given. Similarly with regard to pitch etc. of the self tapping screw as the drawings clearly show the screw. There is, however, one additional feature that would ideally be incorporated in this screw and that would be periodic breaks e.g. in the nature of a longitudinal groove or the like, which will ensure the screw once located in the bone can be held firmly in position against any tendency to rotate by bone that has grown into the appropriate gaps. Persons skilled in the art understand how such non-rotation devices have been used in the past with self tapping screws for bone and the like.

The apparatus of the present invention which is to be used in conjunction with the method is a drill like device which is capable of being mounted in some turning means such as a drill holder. Ideally the apparatus comprises means (1) capable of being located in a predrilled hole or the hole made by the removal of a tooth and a circular skirt or the like means (2) which includes a cutting edge (preferably toothed) (3) capable of removing a plug of the tissue from about the hole in which said means (1) is located. A person skilled in the art will appreciate how such an apparatus can best be used especially bearing in mind the comment to be made in regard to the figures showing the technique of the present invention denoted as 6A to 6E.

Also for use with the present invention would be a postmember capable of being received within the hole in the screw. The hole in the screw (denoted in the drawings by reference numeral 4) could be any particular diameter but is preferably approximately 1.5 to 2 millimeters in diameter for a vitallium screw which is approximately half an inch long.

The technique of the present invention will now be described in detail.

Figure 3:
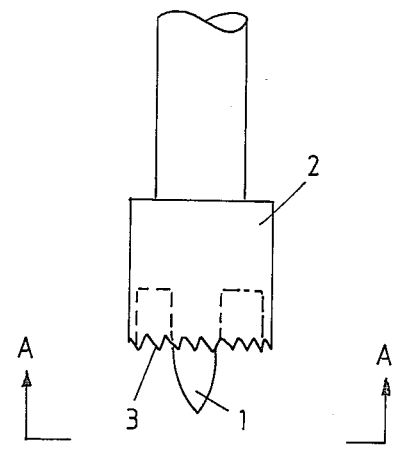
FIG. 3 is a side elevation of the tissue cutting apparatus in accordance with the present invention.

FIG. 6A shows a gap which is to be filled with an artificial tooth between two healthy teeth 5. As a first step a hole 6 is drilled which will accommodate the self tapping screw in accordance with the present invention. This hole is centrally located between the adjacent teeth 5. The soft tissue 7 which overlies the bone 8 then has a plug 9 removed using the plug removing apparatus of the present invention i.e. for this purpose the means 1 (FIG. 3) is located in said hole 6 and the cutter is axially rotated so that the cutting edges 3 thereof cut down to the bone 8 thus enabling a neat plug of the soft tissue to be removed. Ideally the circular collar is approximately 4 to 6 millimeters in diameter so that the same will tightly receive the head of the self tapping screw so as to minimise the risk of gum inflamations and infections.

The next step is to screw in the screw 11 so that the head thereof 11 rests tightly against the bone 8. Shown in FIG. 6C is an axial groove 10 or the like which will assist the alveolar bone to hold the screw firmly in position. Ideally the head of the screw as previously stated is of the Phillips type, however Allen Key type heads or a Pozidriv type of head could be used instead. Persons skilled in the art will appreciate how such a bone screw can be anchored.

The next step, therefore, is to make an impression so that an artificial tooth, for example, formed from a plastic material, can be positioned. The post of the present invention is preferably formed from vitallium, stainless steel or some silver alloy. Other materials however may be employed. The form of the post 13 is such that the same is provided with a bifurcated end and a non-bifurcated end, the non-bifurcated end being such that the same can be received almost completely within the axial hole 4 of the screw as shown in FIG. 6D. Ideally the inner surface of the hole 4 is provided with some roughening, for example a knurl like appearance, as also would the non-bifurcated portion of the post (hereinafter referred to as a risa-post) in order to provide enhanced possibilities of a good grip.

As shown in FIG. 6D the located screw has the risa-post press fitted thereinto and an impression with a normal impression material 14 is made. When this material 14 is taken from the mouth the post 13 comes with it, thereby providing the artificial tooth maker with all that is required so that a plastic tooth 15 can be accurately positioned about the bifurcated end of the risa-post 13. Once the same has been manufactured the same can be fitted permanently in position simply by the application of a dental adhesive so that the post 13 is located firmly as it was located releasably for the taking of the impression within the hole 4 of the vitalium screw.

It can be seen, therefore, that the technique of the present invention does not require any screwing of the risa-post which would lead to difficulties in the actual fitting of the crown etc. owing to the fact that the same should be snug fit between the adjacent teeth 5 which would prevent a rotational fitting.

The proposed technique of the present invention therefore would be conducted in two stages; the first stage would be under a local anaesthetic and would involve steps leading up to the location of the vitalium screw. Such a step would or could include the modification of the bone so as to provide a proper seating for the screw head. The angling of the hole in relation to the alveolar bone is not critical. The second stage may be commenced immediately following the completion of the first stage. This is not the case with existing techniques of the type previously referred to. The second stage would be the stages shown in FIGS. 6D and E. i.e. the location of the risa-post, the taking of the impression and the manufacture and final adhesive fitting of the crown. The dental adhesive that is used is preferably Ames Crown and Bridge Cement.

The advantage of the methods and apparatus of the present invention is primarily the simplicity and speed of the whole procedure. The whole procedure should be relatively cheap as no expensive parts need be used. It is believed, therefore, that the apparatus and methods of the present invention will find wide spread acceptance.

What is claimed is:

1. A dental implant for insertion into a jaw bone, comprising in combination:
   (a) a self-tapping metal screw with a head end and an apex end having an anti-rotation means and including a blind hole extending axially from the head end of said screw, said blind hole including a knurled surface in at least a portion thereof; and
   (b) a metal post member having one end thereof capable of being anchored by adhesive means within said blind hole and the other end being bifurcated and adapted to be attached to a prosthetic tooth.

2. The dental implant as claimed in claim 1, wherein the anti-rotation means is an axially extending groove, extending at least partly along the outer surface of the self-tapping screw.

3. The dental implant as claimed in claim 1, wherein the anti-rotation means is an interruption of the threads in a portion of the outer surface of the self-tapping screw.

4. The dental implant as claimed in claim 1, wherein the self-tapping screw is formed from vitallium.

5. The dental implant as claimed in claim 1, wherein the post member is formed from German Silver.

6. A method of fitting an artificial prosthetic tooth in the mouth of a patient comprising the steps of:
   (a) drilling a hole in the jaw bone at or adjacent the position that the tooth to be replaced had its roots;
   (b) screwing into said hole a screw having a head end and an apex end and being formed from a material compatible with the bone of the jaw bone, said head end having an axial blind hole;
   (c) inserting a post member into said blind hole, said post member being of a length that when received within said blind hole there exists a protruding portion adapted to be wholly received within the prosthetic tooth;
   (d) taking an impression of the space formerly occupied by said tooth to be replaced while said post member is located in said blind hole with an impression material;
   (e) removing said post member and said impression material which is formed onto said protruding portion from the patient and from the shape of said impression material manufacturing the desired artificial tooth; and then
   (f) adhering said post member in said blind hole whereby the formed artificial tooth is located and secured to the jaw bone of the patient.

7. The method as claimed in claim 6, wherein prior to screwing said screw into said hole, a plug of tissue surrounding said hole in the jaw bone is removed to allow countersinking said screw in said hole.

8. The method as claimed in claim 6, wherein said screw is formed from vitallium; said screw has a self-tapping thread; said protruding portion of said post member is bifurcated; and said post member is formed from German Silver.

9. The method as claimed in claim 6, wherein said blind hole of said screw is a non-threaded hole.

10. The method as claimed in claim 9, wherein at least a portion of said blind hole of said screw is provided with a knurl-like surface.

* * * * *